(12) United States Patent
Dai et al.

(10) Patent No.: US 12,402,803 B2
(45) Date of Patent: Sep. 2, 2025

(54) MAGNETIC RESONANCE SYSTEM AND MAGNETIC RESONANCE SCANNING CONTROL METHOD

(71) Applicant: GE Precision Healthcare LLC, Waukesha, WI (US)

(72) Inventors: Qingyu Dai, Beijing (CN); Yuechen Liu, Beijing (CN); Fan Yang, Beijing (CN); Siqing Weng, Beijing (CN); Kun Wang, Beijing (CN)

(73) Assignee: GE Precision Healthcare LLC, Waukesha, WI (US)

( * ) Notice: Subject to any disclaimer, the term of this patent is extended or adjusted under 35 U.S.C. 154(b) by 42 days.

(21) Appl. No.: 18/536,636

(22) Filed: Dec. 12, 2023

(65) Prior Publication Data

US 2024/0215851 A1 Jul. 4, 2024

(30) Foreign Application Priority Data

Dec. 29, 2022 (CN) .......................... 202211710788.6

(51) Int. Cl.
*A61B 5/055* (2006.01)
*A61B 5/00* (2006.01)
*G01R 33/28* (2006.01)

(52) U.S. Cl.
CPC ............ *A61B 5/055* (2013.01); *A61B 5/0035* (2013.01); *A61B 5/0037* (2013.01); *A61B 5/0064* (2013.01); *G01R 33/288* (2013.01)

(58) Field of Classification Search
CPC ...... A61B 5/055; A61B 5/0035; A61B 5/0037; A61B 5/0064; G01R 33/288; G01R 33/283
See application file for complete search history.

(56) References Cited

U.S. PATENT DOCUMENTS

| 10,321,853 | B2 | 6/2019 | Brinker | |
| 2006/0047198 | A1* | 3/2006 | Sugimoto | A61B 5/704 600/410 |
| 2010/0121179 | A1* | 5/2010 | Min | G01R 33/583 600/421 |
| 2013/0261428 | A1* | 10/2013 | Blumhagen | G01R 33/543 600/410 |
| 2015/0268321 | A1* | 9/2015 | Zhai | G01R 33/443 324/309 |
| 2016/0091583 | A1* | 3/2016 | Saybasili | G01R 33/543 600/411 |
| 2016/0113592 | A1* | 4/2016 | Murugappan | A61B 90/90 600/413 |
| 2016/0128606 | A1* | 5/2016 | Sakuragi | G01R 33/288 600/415 |
| 2017/0212913 | A1* | 7/2017 | Kurse | G01R 33/288 |
| 2017/0299667 | A1* | 10/2017 | Bielmeier | G01R 33/543 |

(Continued)

*Primary Examiner* — Sean D Mattson (57) ABSTRACT

Embodiments of the present invention disclose a magnetic resonance system and a magnetic resonance scanning control method, the method including: acquiring a three-dimensional body model of a scan subject; on the basis of the three-dimensional body model, estimating a value of a first body parameter and a value of a second body parameter of the scan subject; and determining a specific absorption rate on the basis of a site to be scanned of the scan subject, the value of the first body parameter and the value of the second body parameter.

9 Claims, 10 Drawing Sheets

(56) References Cited

U.S. PATENT DOCUMENTS

2019/0137580 A1* 5/2019 Lenz .................. G01R 33/3852
2023/0190200 A1* 6/2023 Hölscher ................ A61B 5/744
600/415

* cited by examiner

MAGNETIC RESONANCE SYSTEM AND MAGNETIC RESONANCE SCANNING CONTROL METHOD

CROSS REFERENCE TO RELATED APPLICATIONS

The present application claims priority and benefit of Chinese Patent Application No. 202211710788.6 filed on Dec. 29, 2022, which is incorporated herein by reference in its entirety.

TECHNICAL FIELD

Embodiments of the present invention generally relate to medical imaging technology, and relate in particular to a magnetic resonance (MR) system and a magnetic resonance scanning control method.

BACKGROUND

Magnetic resonance (MR) imaging technology has been widely applied in the field of medical diagnostics, and magnetic resonance systems usually have a main magnet, a gradient drive system, a gradient coil assembly, a radio frequency transmit chain module, a radio frequency receive chain module, etc. The radio frequency transmit chain module is used to generate radio frequency pulses to excite a subject to generate a magnetic resonance signal, and a medical image can be reconstructed using the magnetic resonance signal.

A specific absorption ratio (SAR) of radio frequency energy is an important reference indicator in the transmit chain module, and shows the ratio of radio frequency signals absorbed by the scan subject. The SAR value is usually set below a certain threshold to avoid injury to the subject during a scanning process. The setting of SAR values has more stringent limitations when patients having implants are undergoing magnetic resonance imaging. For example, some types of implants have very low SAR limits.

In the prior art, the SAR value is usually determined on the basis of the weight of the subject. Energy absorption still varies for different individuals of the same weight, however, due to safety considerations, the SAR value can only be set to a minimum/relatively low limit, so that the radio frequency power is limited to a relatively low value, thus affecting scanning efficiency and imaging quality.

SUMMARY

Provided in one aspect of the present invention are a magnetic resonance system and a magnetic resonance scanning control method, the method comprising: acquiring a three-dimensional body model of a scan subject; on the basis of the three-dimensional body model, estimating a value of a first body parameter and a value of a second body parameter of the scan subject; and determining a specific absorption rate on the basis of a site to be scanned of the scan subject, the value of the first body parameter and the value of the second body parameter.

Provided in another aspect of the present invention is a magnetic resonance scanning control method for a magnetic resonance system, the magnetic resonance system comprising a scanning table and a camera, and the method comprising: acquiring, by means of the camera, a three-dimensional profile image of a scan subject on the scanning table; acquiring a three-dimensional body model of the scan subject on the basis of the three-dimensional profile image; estimating the weight and height of the scan subject on the basis of the three-dimensional body model; receiving a user operation instruction so as to determine a site to be scanned in the three-dimensional body model; and determining a specific absorption rate on the basis of the determined site to be scanned, the weight, and the height.

Another aspect of the present invention provides a magnetic resonance system, including: a main magnet, a radio frequency coil assembly, a gradient coil assembly, and a scanning table for bearing a scan subject; a sequence pulse generator used to generate a scan sequence, the scan sequence comprising radio frequency transmission pulses; a three-dimensional imaging apparatus; and a scanning controller comprising operation instructions, the operation instructions being used for performing the following steps of: receiving a three-dimensional profile image of the scan subject acquired by means of the three-dimensional imaging apparatus; acquiring a three-dimensional body model of the scan subject on the basis of the three-dimensional profile image; estimating, on the basis of the three-dimensional body model, a value of a first body parameter and a value of a second body parameter of the scan subject; and determining a specific absorption rate on the basis of a site to be scanned of the scan subject, the value of the first body parameter, and the value of the second body parameter.

BRIEF DESCRIPTION OF THE DRAWINGS

The described and other features, aspects, and advantages of the present invention will be better understood once the following detailed description has been read with reference to the accompanying drawings. In the accompanying drawings, the same reference signs are used to represent the same components throughout the accompanying drawings, in which.

DETAILED DESCRIPTION

Specific embodiments of the present invention will be described in detail below with reference to the accompanying drawings in order to assist those skilled in the art to understand exactly the subject matter set forth in the present invention. In the following detailed description of the following specific embodiments, the present specification does not describe in detail any known functions or configurations to prevent unnecessary details from affecting the disclosure of the present invention.

Unless otherwise defined, the technical or scientific terms used in the claims and the description should be as they are usually understood by those possessing ordinary skill in the technical field to which they belong. Terms such as "first", "second" and similar terms used in the present description and claims do not denote any order, quantity, or importance, but are only intended to distinguish different constituents. The terms "one" or "a/an" and similar terms do not express a limitation of quantity, but rather that at least one is present. The terms "include" or "comprise" and similar words indicate that an element or object preceding the terms "include" or "comprise" encompasses elements or objects and equivalent elements thereof listed after the terms "include" or "comprise", and do not exclude other elements or objects. The terms "connect" or "link" and similar words are not limited to physical or mechanical connections, and are not limited to direct or indirect connections. Furthermore, it should be understood that references to "an embodiment" or "embodiments" of the present disclosure are not intended to be construed as excluding the existence of additional implementations that also incorporate the referenced features.

A "module", "unit", etc., as described herein may be implemented by using software, hardware, or a combination of software and hardware. For example, in accordance with some aspects of the embodiments of the present invention, the "modules" described herein may be implemented as computer program modules or circuit modules.

An "image" described herein may include a displayed image, or may include data that forms the displayed image.

Figure 1:
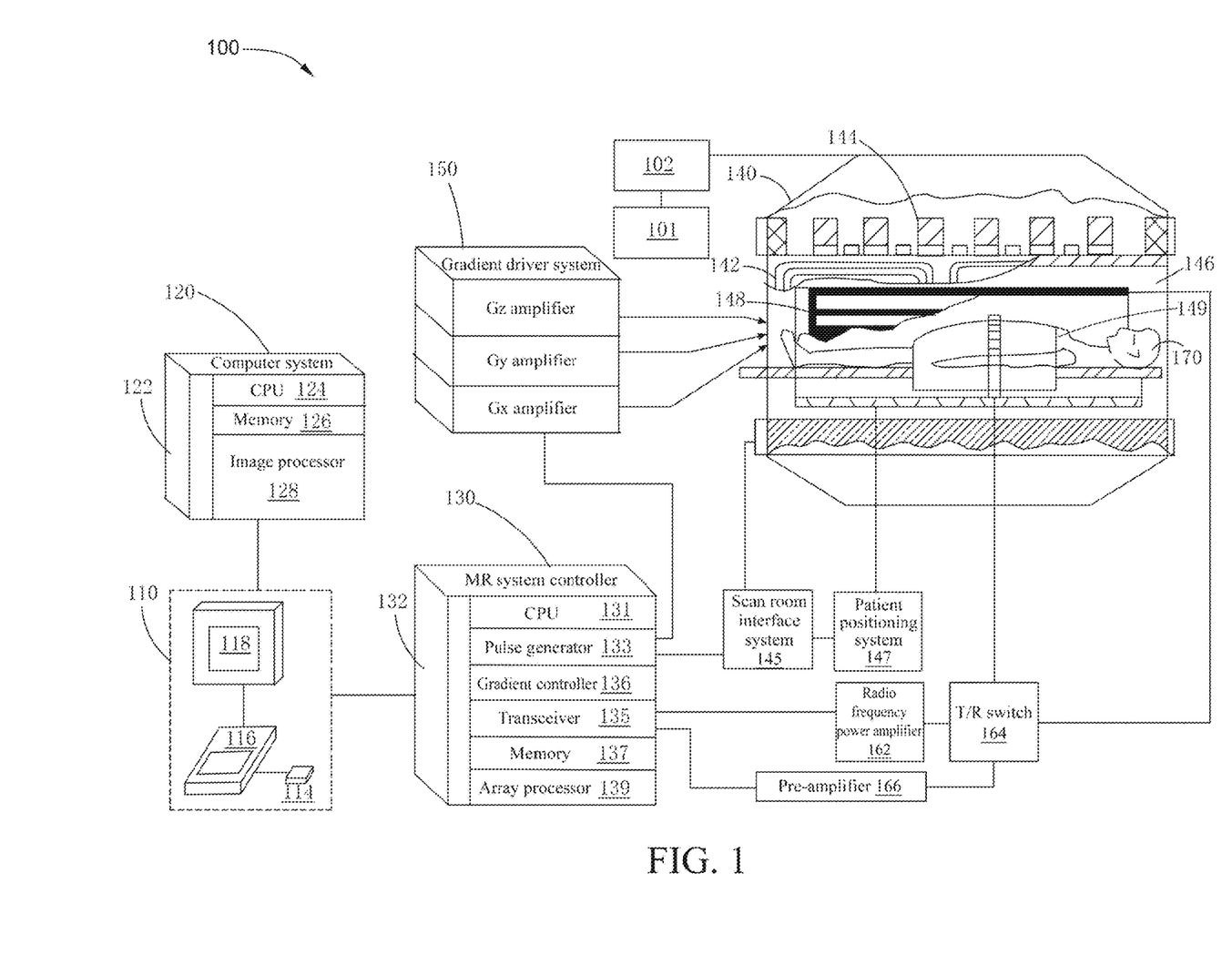
FIG. 1 illustrates an exemplary magnetic resonance (MR) system according to some embodiments of the present invention.

Referring to FIG. 1, an exemplary magnetic resonance (MR) system 100 according to some embodiments of the present invention is illustrated. An operator workstation 110 is used to control the operation of the MR system 100, the operator workstation 110 including an input apparatus 114, a control panel 116, and a display 118. The input apparatus 114 may be a joystick, a keyboard, a mouse, a trackball, a touch-activated screen, voice control, or any similar or equivalent input apparatus. The control panel 116 may include a keyboard, a touch-activated screen, voice control, a button, a slider, or any similar or equivalent control apparatus. The operator workstation 110 is coupled to and communicates with a computer system 120, and provides an interface to allow an operator to plan a magnetic resonance scan, display an image, perform image processing, and store data and images.

The computer system 120 includes a plurality of modules that communicate with one another by means of an electrical and/or data connection module 122. The connection module 122 may be a wired communication link, an optical fiber communication link, a wireless communication link, and the like. The computer system 120 may include a central processing unit (CPU) 124, a memory 126, and an image processor 128. In some embodiments, the image processor 128 may be replaced by an image processing function run in the CPU 124. The computer system 120 may be connected to an archive media apparatus, a persistent or backup memory, or a network. The computer system 120 may be coupled to and communicates with a separate MR system controller 130.

The MR system controller 130 includes a set of modules that communicate with one another by means of an electrical and/or data connection module 132. The connection module 132 may be a direct wired communication link, an optical fiber communication link, a wireless communication link, and the like. In an alternative embodiment, modules of the computer system 120 and the MR system controller 130 may be implemented on the same computer system or on a plurality of computer systems. The MR system controller 130 may include a CPU 131, a sequence pulse generator 133 that communicates with the operator workstation 110, a transceiver (or an RF transceiver) 135, a gradient controller 136, a memory 137, and an array processor 139.

A subject 170 of the MR scan may be positioned within a cylindrical imaging volume 146 of a magnetic resonance assembly 140 via a scanning table, and the subject 170 may have one or more implants in the body thereof. The MR system controller 130 controls the scanning table to travel along the Z-axis direction of the magnetic resonance system, so as to deliver the subject 170 into the imaging volume 146. The magnetic resonance assembly 140 includes a superconducting magnet having a superconducting coil 144, a radio frequency (RF) coil assembly, and a gradient coil assembly 142. The superconducting coil 144 has a magnet aperture to form the cylindrical imaging volume 146. During operation, the superconducting coil 144 provides a static uniform longitudinal magnetic field $B_0$ throughout the cylindrical imaging volume 146. The radio frequency coil assembly may include a body coil 148 and a surface coil 149, and may be used to send and/or receive a radio frequency signal.

The MR system controller 130 may receive a command from the operator workstation 110 to indicate an MRI scan sequence that is to be executed during the MRI scan. The "scan sequence" above refers to a combination of pulses that have specific intensities, shapes, time sequences, and the like and that are applied when a magnetic resonance imaging scan is executed. The pulses may typically include, for example, a radio frequency pulse and a gradient pulse. A plurality of scan sequences may be pre-stored in the computer system 120, so that a sequence suitable for clinical examination requirements can be indicated by means of the operator workstation. The clinical examination requirements may include, for example, an imaging site, an imaging function, an imaging effect, scanning safety and the like. The sequence pulse generator 133 of the MR system controller 130 sends, on the basis of the indicated sequence, an instruction describing the time sequences, intensities, and shapes of the radio frequency pulse and gradient pulse in the sequence so as to operate a system component that executes the sequence.

A radio frequency pulse in the scan sequence sent by the pulse generator 133 may be generated by the transceiver 135, and the radio frequency pulse is amplified by a radio frequency power amplifier 162. The amplified radio frequency pulse is provided to the body coil 148 via a transmit/receive switch (T/R switch) 164, and the RF body coil 148 then immediately provides a transverse magnetic field $B_1$. As a non-limiting example, a transmitting portion of the transceiver 135, the radio frequency power amplifier 162, the T/R switch 164, and the like constitute at least a portion of a radio frequency transmit link. The transverse magnetic field $B_1$ is substantially perpendicular to $B_0$ throughout the cylindrical imaging volume 146, and the transverse magnetic field $B_1$ is used to excite stimulated nuclei within the body of the scan subject, thereby generating an MR signal.

A portion of the energy loaded by the radio frequency pulse is released in the form of heat which is absorbed by the human body, and over time, the energy is deposited at a scan site of the human body, thereby resulting in a local or systemic temperature increase of the human body. The energy that can be absorbed per unit of time and per unit of body weight is defined as SAR, and different SAR values are usually set for different parts of the body.

The gradient pulse in the scan sequence sent by the pulse generator 133 may be generated by the gradient controller 136 and acts on a gradient driver 150. The gradient driver 150 includes $G_x$, $G_y$, and $G_z$ amplifiers, and the like. Each of the $G_x$, $G_y$, and $G_z$ gradient amplifiers is used to excite a corresponding gradient coil in the gradient coil assembly 142, so as to generate a magnetic field gradient used to spatially encode an MR signal during an MR scan.

The pulse generator 133 is coupled to and communicates with a scan room interface system 145, and the scan room interface system 145 can receive signals from various sensors associated with the state of the magnetic resonance assembly 140 and various processors provided in a scan room. The scan room interface system 145 is further coupled to and communicates with a patient positioning system 147, the patient positioning system 147 sending and receiving a signal to control the scanning table to travel so as to transport the patient or the subject 170 to a desired position to perform the MR scan.

As described above, the RF body coil 148 and the RF surface coil 149 may be used to transmit a radio frequency pulse and/or receive MR signals from the scan subject. The MR signals emitted by excited nuclei in the body of the scan subject may be sensed and received by the RF body coil 148 or the RF surface coil 149 and then sent back to a preamplifier 166 by means of the T/R switch 164. The T/R switch 164 may be controlled by a signal from the MR system controller 130 to electrically connect, during a transmit mode, the radio frequency power amplifier 162 to the RF body coil 148 and to connect, during a receive mode, the preamplifier 166 to the RF body coil 148. The T/R switch 164 may further enable the RF surface coil 149 to be used in the transmit mode or the receive mode.

In some embodiments, the MR signals sensed and received by the RF body coil 148 or the RF surface coil 149 and amplified by the preamplifier 166 are demodulated, filtered, and digitized in a receiving portion of the transceiver 135, and transmitted as a raw k-space data array to the memory 137 in the MR system controller 130.

A reconstructed magnetic resonance image may be obtained by transforming/processing the stored raw k-space data. For each image to be reconstructed, the data is rearranged into separate k-space data arrays, and each of the separate k-space data arrays is inputted into the array processor 139, the array processor being operated to transform the data into an array of image data.

The array processor 139 uses transform methods, most commonly Fourier transform, to create images from the received MR signals. These images are transmitted to the computer system 120 and stored in the memory 126. In response to commands received from the operator workstation 110, the image data may be stored in a long-term memory, or may be further processed by the image processor 128 and transmitted to the operator workstation 110 for presentation on the display 118.

In various embodiments, components of the computer system 120 and MR system controller 130 may be implemented on the same computer system or on a plurality of computer systems. It should be understood that the MR system 100 shown in FIG. 1 is intended for illustration. Suitable MR systems may include more, fewer, and/or different components.

The MR system controller 130 and the image processor 128 may separately or collectively include a computer processor and a storage medium. The storage medium records a program for predetermined data processing that is to be executed by the computer processor. For example, the storage medium may store a program used to implement scanning processing (such as a scan flow and an imaging sequence), image reconstruction, image processing, and the like. Specifically, the storage medium may store the magnetic resonance scanning control method of any of the embodiments of the present invention. The described storage medium may include, for example, a ROM, a floppy disk, a hard disk, an optical disk, a magneto-optical disk, a CD-ROM, or a non-volatile memory card.

With continued reference to FIG. 1, in embodiments of the present invention, a scan controller 101 is provided, used to control the magnetic resonance system to perform the magnetic resonance scanning control method of the present invention so as to more accurately set radio frequency parameters during a magnetic resonance scan when there is an implant, enabling a more appropriate radio frequency power to be provided while performing a safe scan. In some embodiments, the scanning controller 101 may be integrated in the MR system controller 130 or the computer system 120, or may be independently provided.

In embodiments of the present invention, a three-dimensional image acquisition device 102 may also be provided for acquiring a three-dimensional profile image of the scan subject positioned on the scanning table. The scanning controller 101 may utilize the three-dimensional profile image to acquire a three-dimensional body model of the scan subject, and estimate at least two body parameters of the subject on the basis of the three-dimensional body model, may determine, on the basis of the three-dimensional body model, a site to be scanned, and may further input an implant location on the basis of the operation of the three-dimensional body model, and determine a root mean square value B+rms of a radio frequency field on the basis of the implant location and the site to be scanned. The foregoing will be described in detail below.

In one embodiment, the three-dimensional image acquisition device 102 may include hardware devices, such as a camera, a TOF (time-of-flight) sensor, a laser scanner, etc., disposed on a magnetic resonance assembly housing (or a magnet housing), wherein the camera may include a depth video camera or a two-dimensional video camera.

Figure 2:
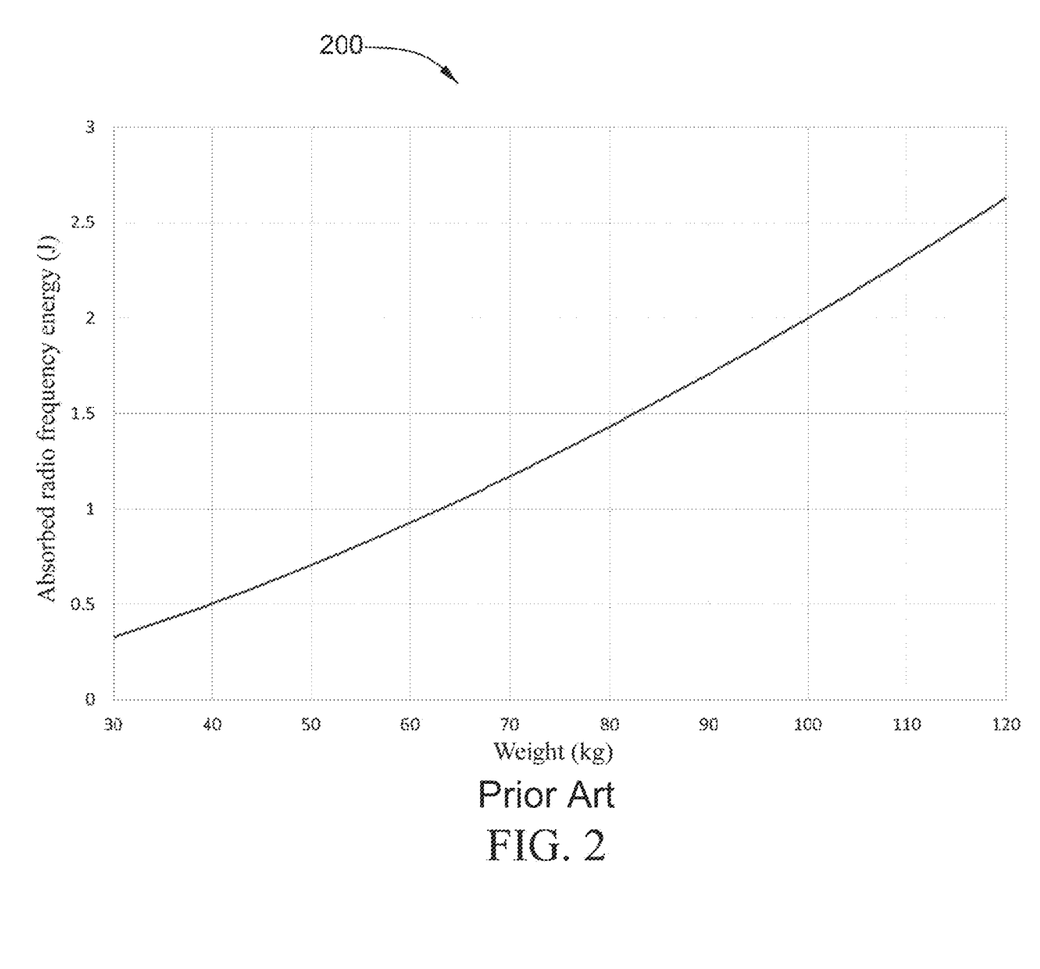
FIG. 2 schematically illustrates energy prediction curves in the prior art.

Referring to FIG. 2, an energy prediction curve, also referred to as a $J_{std}$ model, in the prior art is schematically illustrated. The horizontal axis represents human body weight and the vertical axis represents standard absorbed radio frequency energy. In the prior art, before performing a magnetic resonance scan on a patient, the weight of the patient is acquired and inputted into the magnetic resonance system, and when performing scan parameter setting, a standard absorbed radio frequency energy is acquired on the basis of the inputted weight information, and an SAR value is set on the basis of the standard absorbed radio frequency energy. As described above, this means is not conducive to precise control of radio frequency power. In addition, since the weight information needs to be manually inputted, the foregoing means is not beneficial for simplifying the scanning process.

Figure 3:
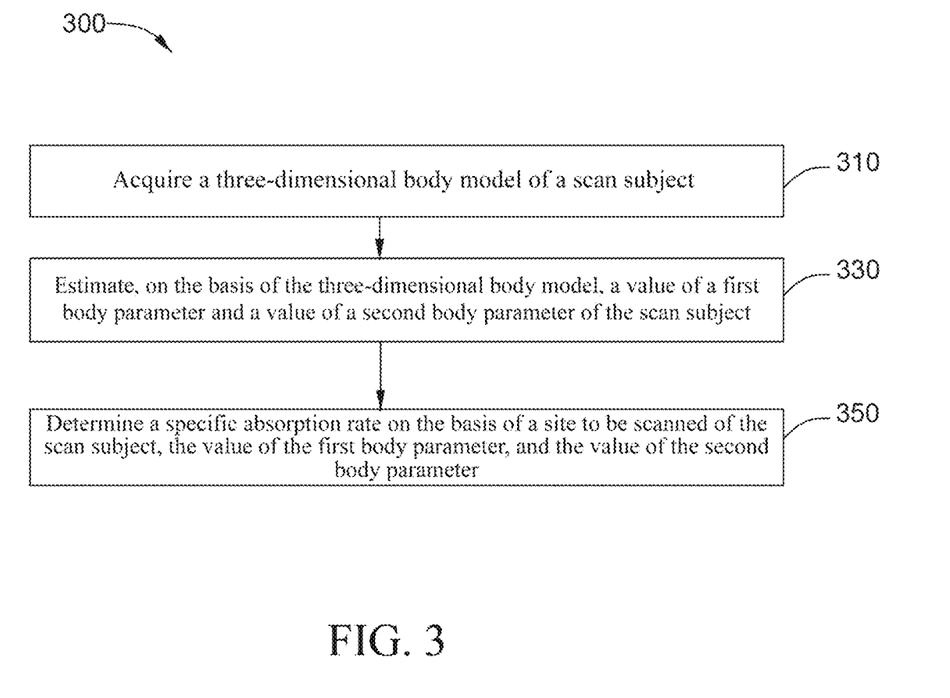
FIG. 3 illustrates a flowchart of a magnetic resonance scanning control method according to an embodiment of the present invention.

With reference to FIG. 3, a flowchart 300 of a magnetic resonance scanning control method of an embodiment of the present invention is illustrated.

Figure 7:
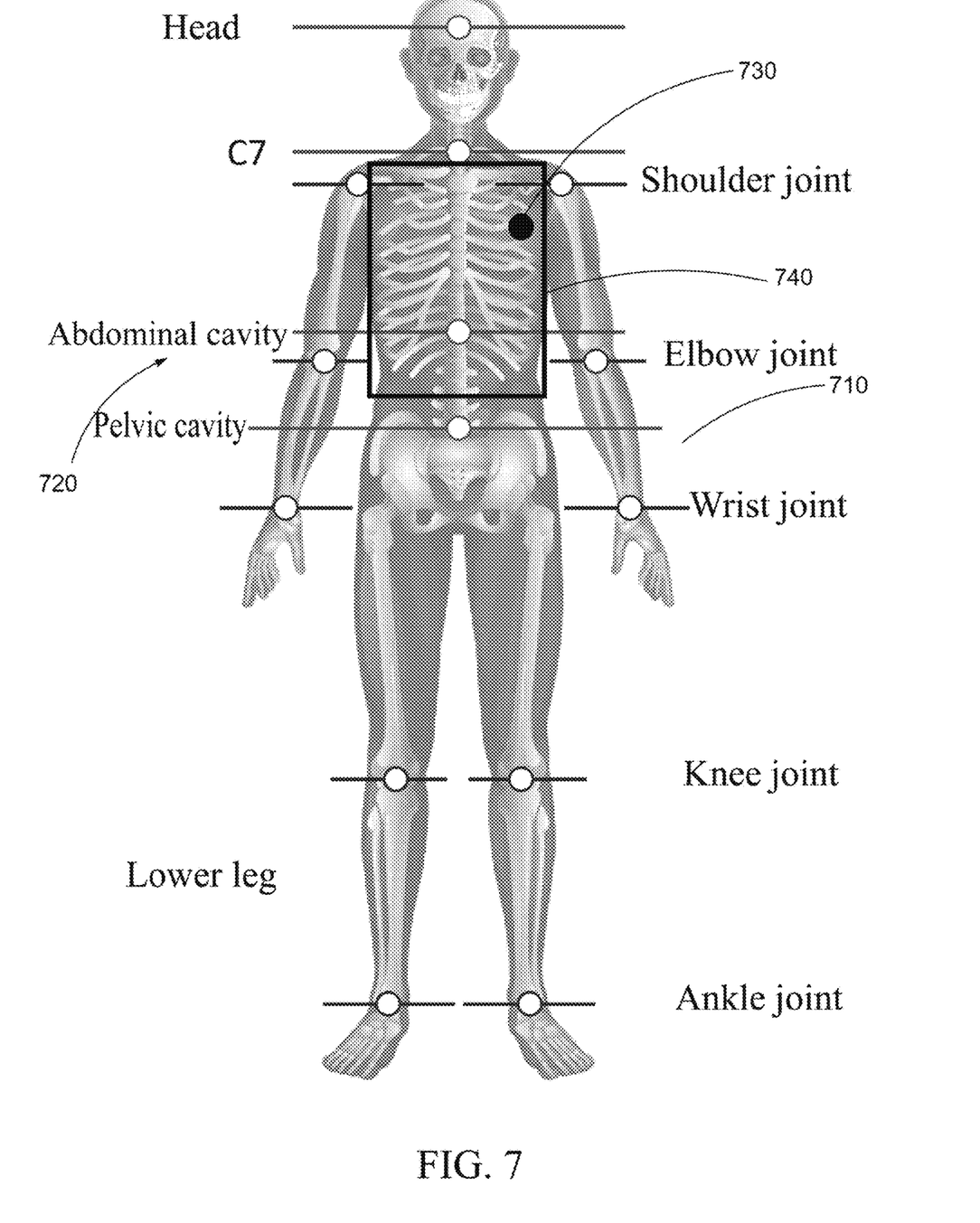
FIG. 7 illustrates a three-dimensional body model of an example of the present invention.

In step 310, a three-dimensional body model of a scan subject is acquired. An example of the three-dimensional body model may be as shown in FIG. 7. The "three-dimensional body model of the scan subject" described in the present step varies at least due to different heights and weights of scan subjects, and may also vary due to other information related to height or weight (e.g., gender, age, body proportions, physical features, etc.). In some embodiments, the three-dimensional body model may include a body portion 710, e.g., the body portion 710 may have a basic human body structure including, but not limited to, a torso, limbs, a head, a brain, a heart, a liver, a spleen, a stomach, bones, and the like. The three-dimensional body model may further include an information labeling portion 720, such as highlighting and displaying specific locations of the body portion 710 by computer-assisted means, such as major joints, specific bone locations, and the like, and these labeled sites may be further annotated using text. In some embodiments, the three-dimensional body model may have a more simplified structure, e.g., may include only an outer contour, and a physician may operate in the simplified three-dimensional body model on the basis of their own knowledge of human anatomy.

In step 330, a value of a first body parameter and a value of a second body parameter of the scan subject are estimated on the basis of the three-dimensional body model. The first body parameter may include weight, and the second body parameter may include height or any other physiological parameter that can directly or indirectly indicate height, including, but not limited to, gender, age, body proportions, physical characteristics, and the like, as described above.

In step 350, a specific absorption rate, i.e., SAR, is determined on the basis of the site to be scanned of the scan subject, the value of the first body parameter, and the value of the second body parameter.

In the embodiment of the present invention, two body parameters are simultaneously estimated by means of acquiring the three-dimensional body model of the subject, which avoids process redundancy and possible input errors caused by manually inputting the parameters, enhancing the automation of the scanning process. Furthermore, by means of determining the specific absorption rate on the basis of two body parameters, the accuracy of the setting of scanning parameters can be improved compared with setting a specific absorption rate only using a single parameter, enabling more accurate control of the radio frequency power and ensuring imaging efficiency and the image quality while performing a safe scan.

Figure 4:
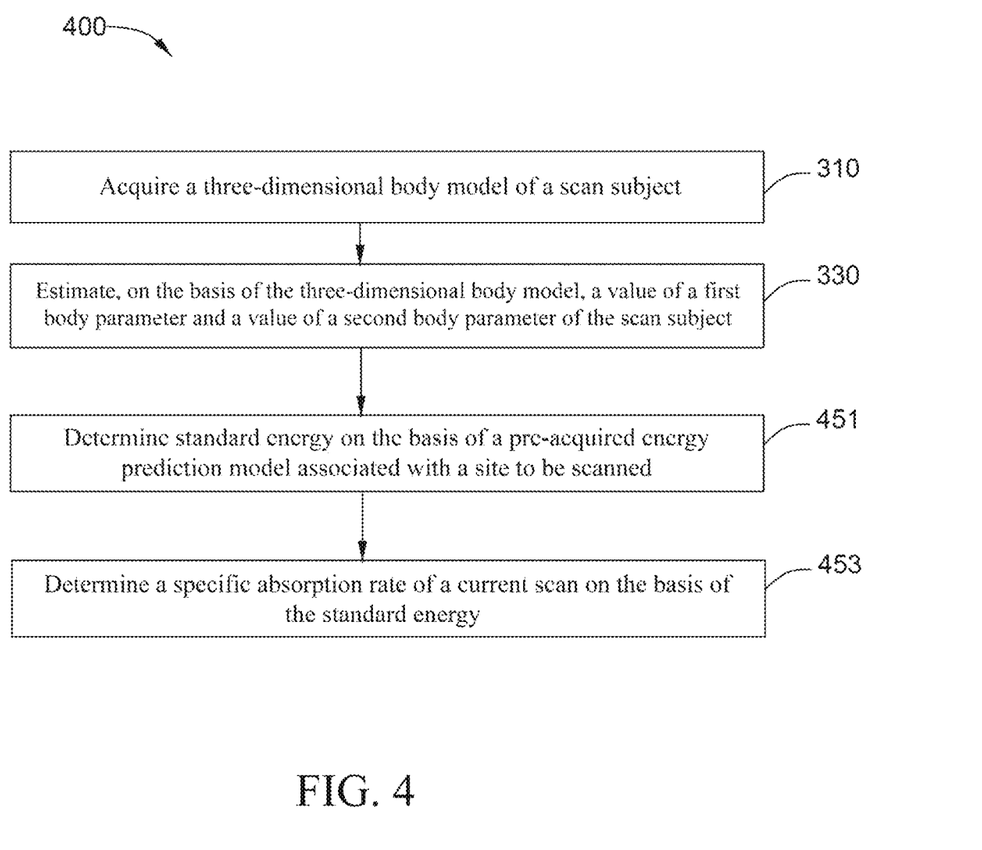
FIG. 4 illustrates a flowchart of a magnetic resonance scanning control method according to another embodiment of the present invention.
Figure 5:
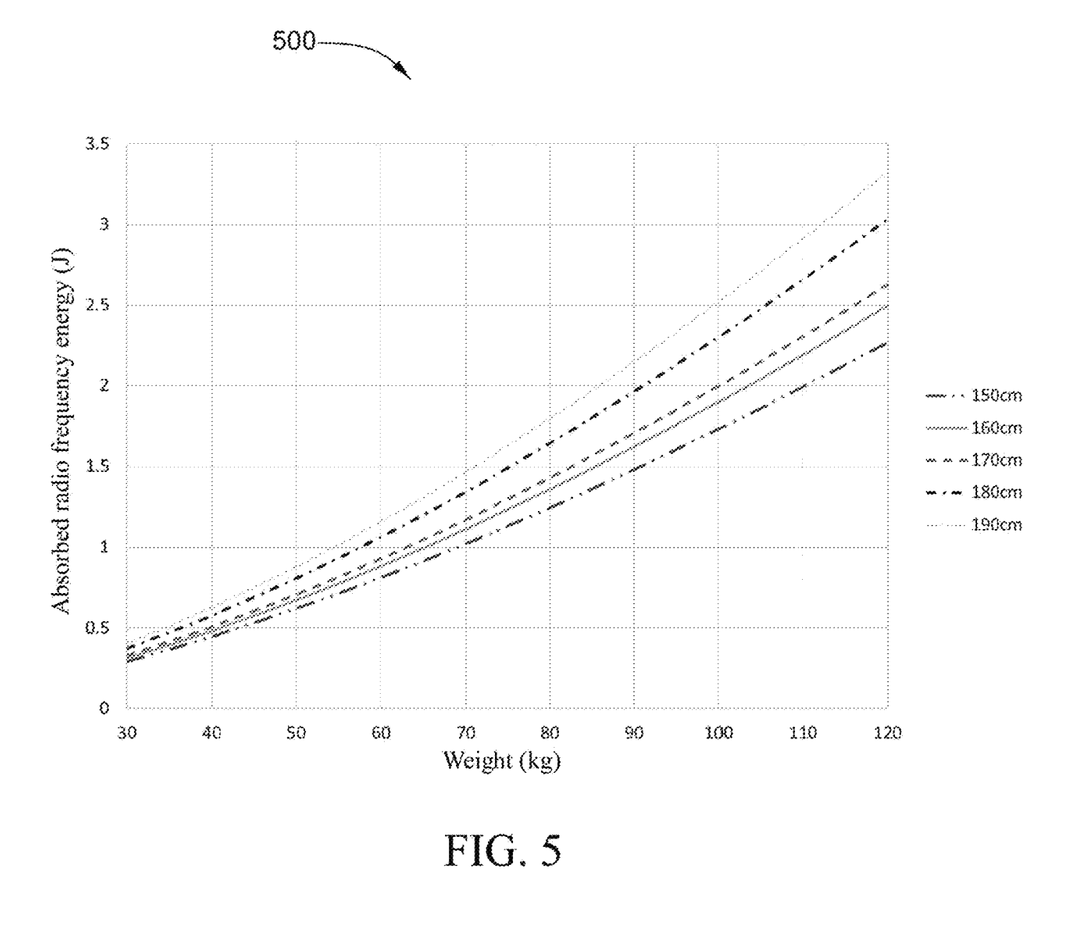
FIG. 5 illustrates an example energy prediction model of the present invention.

Referring to FIG. 4, a flowchart 400 of a magnetic resonance scanning control method of another embodiment of the present invention is illustrated; in step 451, a standard energy is determined on the basis of a pre-acquired energy prediction model associated with the site to be scanned, and in step 453, a specific absorption rate of the current scan is determined on the basis of the standard energy. The standard energy may be an absorbed radio frequency energy as shown in FIG. 5. As described, different body parts usually have different SAR value settings, e.g., head SAR value, abdominal SAR value, chest SAR value, whole body SAR value, etc., and thus the energy prediction model used in step 451 may also be automatically called according to the setting of the site to be scanned.

Referring to FIG. 5, an example energy prediction model 500 of the present invention is illustrated, wherein the energy prediction model 500 may be an optimized model determined on the basis of one or more magnetic resonance scans of a volunteer, having optimized standard energy, i.e., an absorbed radio frequency energy value as shown in FIG. 5, for individuals having different heights and weights, thus the SAR and the SAR-related scanning parameters can be determined on the basis of the optimized absorbed radio frequency energy value. The energy prediction model 500 may be used to represent the correspondence relationship of the standard energy with different values of the first body parameter and different values of the second body parameter, e.g., in the prediction model 500, the standard energy has both weight and height as variables. For example, FIG. 5 illustrates a plurality of curves, each curve corresponding to a different height (e.g., heights of 150 cm, 160 cm, 170 cm, 180 cm, and 190 cm, respectively), and the standard energy of each curve again varies with changes in weight. The statistical graph shown in FIG. 5 is only one example means of representation of the energy prediction model 500, and other types of graphs may be used to represent the energy prediction model 500. In other examples, curves can be set for more height values. In other examples, a plurality of corresponding curves may be set for different body parts of the same height. The described "standard energy" refers to the radio frequency energy within a unit of time when a radio frequency wave of a specific shape is emitted, and a person skilled in the art would understand that the standard energy can be converted to the specific absorbed energy of the current scan on the basis of a preset operation, i.e., the specific absorption rate described above. For example, an operation coefficient of the standard energy can be determined on the basis of the shape of the radio frequency wave used in the current scan.

Figure 6:
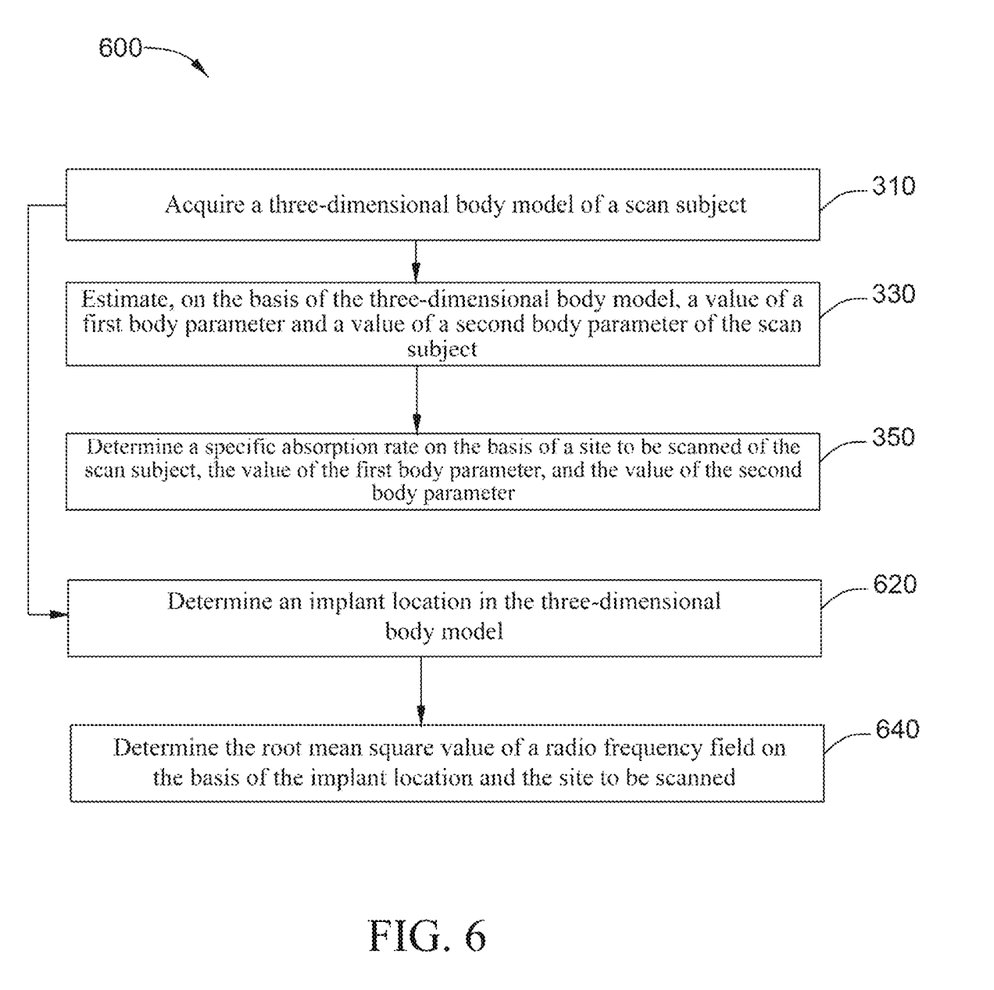
FIG. 6 illustrates a flowchart of a magnetic resonance scanning control method provided by another embodiment of the present invention.

Referring to FIG. 6, a flowchart 600 of a magnetic resonance scanning control method provided by another embodiment of the present invention is illustrated. In step 620, an implant location, such as the implant location 730 as shown in FIG. 7, is determined in the three-dimensional body model. In step 640, the root mean square value (B+rms) of the radio frequency field is determined on the basis of the implant location and the site to be scanned.

For example, for some locations (types) or brands of implants, according to the scan region or the scan range, there are specific requirements for the radio frequency field root mean square value, e.g., there is a cardiac pacemaker that requires that the radio frequency field root mean square value B+rms be less than or equal to 2.8 microteslas (uT) when the region of the magnetic resonance scan (or the site to be scanned) is below the cervical spine at the C7 vertebra. Therefore, if it is determined that such an implant is placed at the subject's heart, and it is determined, according to the set site to be scanned, that the scan region is below the C7 location, then the radio frequency field root mean square value is set at or below 2.8 uT.

In this way, the energy of the radio frequency pulse is directly controlled within the range required by the implant in a fast and automated process, to achieve a safe scan.

The basic information of the implant may be received by an operator by a variety of means; for example, it may be manually inputted by the user, or may be automatically acquired by the system on the basis of a historical scan record of the scan subject, or may be obtained from an electronic medical record of the scan subject on the basis of a network-interconnected medical institution or medical device. When the basic information of the implant is acquired, then the radio frequency parameter (e.g., the radio frequency field root mean square value) requirements of the implant for different scan regions can be known.

The operator may determine the location of the implant in the three-dimensional body model on the basis of pre-acquired basic information of the implant and location information thereof in the body of the scan subject; the location of the implant may also be directly determined by means of labeling the implant in the three-dimensional body model. The basic information of the implant may include one or a plurality of implantation location information (e.g., the body part where the implant is located), the type of implant, the size, the manufacturer, and a range of safety parameters for the implant. The implantation location information may be related to the function or location of the implant. For example, a cardiac pacemaker, a cardiac stent, etc., may be related to the heart, and a nerve stimulator may be related to the brain, or other locations of the body. The range of safety parameters may include the maximum SAR value that can be withstood, and may further include specific requirements for radio frequency field root mean square values in different scanning regions, which may be defined by the manufacturer of the implant and retrieved or inputted through the magnetic resonance system.

The site to be scanned may be set in the magnetic resonance system on the basis of conventional means, such as on the basis of a scanning site inputted by an operator, and when step 640 is performed, corresponding position mapping is automatically performed in the three-dimensional body model on the basis of the inputted scanning site, and may be determined directly in the three-dimensional body model, as will be illustrated, for example, with reference to FIG. 7.

Referring to FIG. 7, a schematic diagram of determining a site to be scanned of a scan subject in a three-dimensional body model is shown. Specifically, the three-dimensional body model may be displayed by means of a graphical user interface, and an operator may select, by means of a computer-assisted operation tool, a region to be imaged and scanned in the three-dimensional body model as the site to be scanned 740. After the scan site 740 is determined, step 350 can be performed, e.g., determining the specific absorption rate on the basis of the site to be scanned as well as the height and weight, and further, after the scan site 740 is determined, step 640 can be performed, e.g., determining a set value for the root mean square value of the radio frequency field in view of the corresponding requirements of the implant.

The magnetic resonance system can automatically adjust the waveform of the radio frequency pulse according to the determined SAR value and the root mean square value of the radio frequency field so that the above settings are satisfied.

Figure 8:
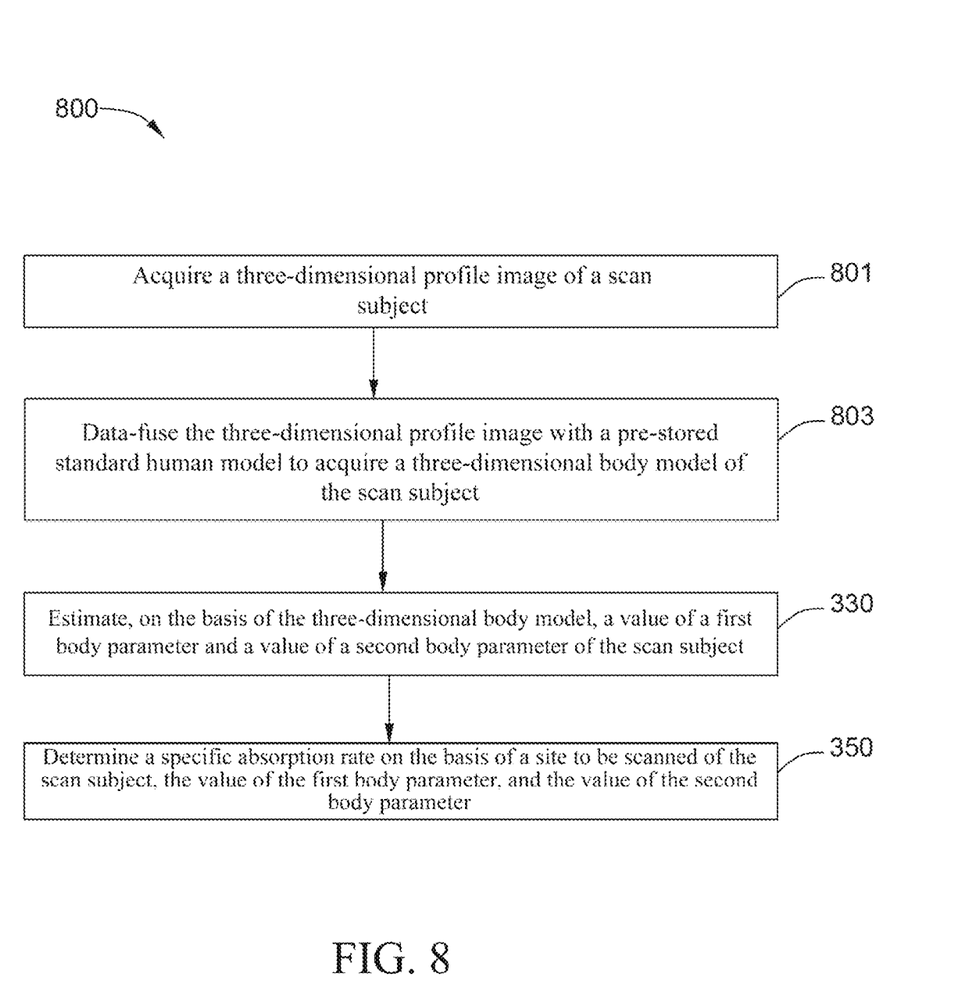
FIG. 8 illustrates a flowchart of a magnetic resonance scanning control method of another embodiment of the present invention.

Referring to FIG. 8, a flowchart 800 of a magnetic resonance scanning control method of another embodiment of the present invention is illustrated, wherein the steps of acquiring a three-dimensional body model are illustrated in a more specific manner. In step 801, three-dimensional profile information of the scan subject is acquired. For example, a scan subject positioned on a scanning table may be photographed by means of a camera to acquire a three-dimensional profile image of the scan subject. The camera may for example, be a depth video camera. Optionally, the camera may also include a two-dimensional video camera, and the three-dimensional profile image may be obtained based on a two-dimensional image taken by the two-dimensional video camera, for example, by means of image processing. By means of the camera, an image of the current scan subject can be obtained more accurately and in real time to enable subsequent generation, on the basis of the three-dimensional profile image, of a simulated scan subject more closely matching the real scan subject, thereby estimating more accurate body parameters.

In other embodiments, the three-dimensional profile image of the scan subject may also be acquired by means of, for example, a time-of-flight (TOF) sensor, a laser scanner, or another device.

In step 803, the three-dimensional profile image is data fused with a pre-stored standard human body model to acquire a three-dimensional body model of the scan subject, wherein the standard human body model includes a basic human body structure. The standard human body model may include a plurality of models based on different ages, genders, body types, and so on.

By means of performing the described data fusion, the obtained three-dimensional body model not only has conventional anatomical structures of the human body, but may also be individually varied on the basis of different individuals, such that the obtained three-dimensional body model is sufficiently close to the body structure of the real scan subject, which facilitates subsequent correct body parameter estimation and location labeling, etc.

Furthermore, the three-dimensional profile image of the scan subject and the standard human model may be matched based on preset weight information of different body parts. In this way, it is avoided that the same proportion is simply used to make variations and matches on all body parts, enabling the obtained model to be closer to reality. For example, for an obese scan subject, compared with the standard model, changes to the limbs are larger, while changes to the heart are smaller. Therefore, the weight of the limbs may be larger, and the weight of the heart may be smaller.

Figure 9:
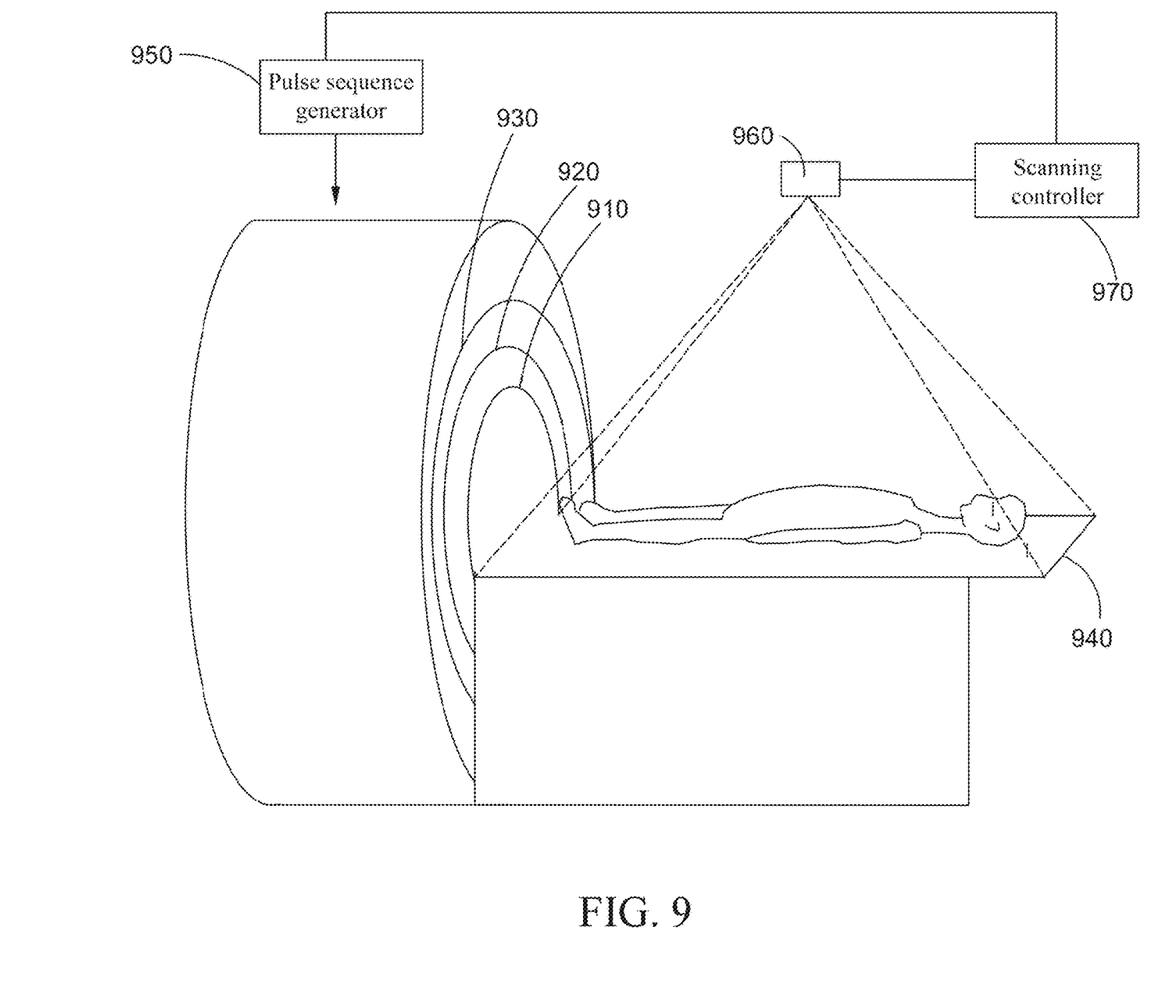
FIG. 9 illustrates a schematic diagram of a magnetic resonance system of another embodiment of the present invention.

FIG. 9 illustrates an example of a magnetic resonance system of the present invention, which may include at least some of the components of the system 100 shown in FIG. 1. Specifically, the magnetic resonance system may include a main magnet 910, a radio frequency coil assembly 920, a gradient coil assembly 930, a scanning table 940 for bearing a scan subject, a sequence pulse generator 950, a camera 960, and a scan controller 970. The sequence pulse generator 950 is used to generate a scan sequence that includes radio frequency transmission pulses.

The camera 960 may be positioned relative to the scanning table 940 to be able to photograph a scan subject located on the scanning table 940. Specifically, the camera 960 may be mounted so as to be located above the scanning table 940. In some embodiments, the camera 960 may be fixed on a housing of the main magnet 910 by means of a bracket.

The camera 960 is used to acquire three-dimensional profile information of the scan subject. The scanning controller 970 includes operational instructions for performing the magnetic resonance scanning control method of any embodiment of the present invention. For example, the operational instructions are used for: receiving a three-dimensional profile image of the scan subject acquired via the three-dimensional imaging apparatus; acquiring a three-dimensional body model of the scan subject on the basis of the three-dimensional profile image; estimating a value of a first body parameter and a value of a second body parameter of the scan subject on the basis of the three-dimensional body model; and determining a specific absorption rate on the basis of a site to be scanned of the scan subject, the value of the first body parameter, and the value of the second body parameter.

Furthermore, the operation instructions are also used for: determining an implant location in the three-dimensional body model; and determining the root mean square value of the radio frequency field on the basis of the implant location and the site to be scanned of the scan subject.

In an alternative solution of the above example, the three-dimensional profile image of the scan subject may also be acquired using other means, at which point a depth video camera may not need to be mounted, or another three-dimensional image acquisition apparatus may be mounted.

Figure 10:
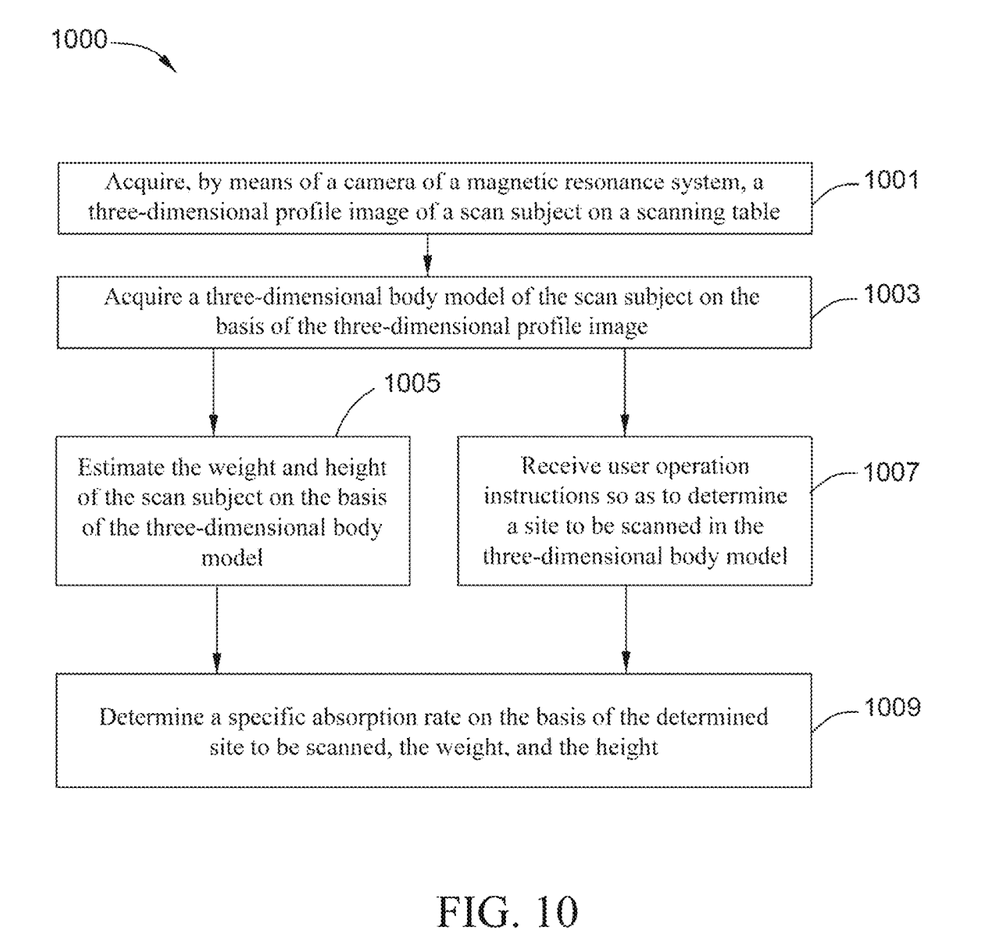
FIG. 10 illustrates a flowchart of a magnetic resonance scanning control method of another embodiment of the present invention.

FIG. 10 illustrates a flowchart 1000 of a magnetic resonance scanning control method of another embodiment of the present invention, wherein, in step 1001, a three-dimensional profile image of a scan subject on the scanning table 940 is acquired via the camera 960; in step 1003, a three-dimensional body model of the scan subject is acquired on the basis of the three-dimensional profile image; in step 1005, the weight and height of the scan subject are estimated on the basis of the three-dimensional body model; in step 1007, a user operation instruction is received so as to determine a site to be scanned in the three-dimensional body model; and in step 1009, a specific absorption rate is determined on the basis of the determined site to be scanned, the weight, and the height.

Furthermore, the method may also include: receiving user operation instructions so as to determine an implant location in the three-dimensional body model; and, determining the root mean square value of the radio frequency field on the basis of the implant location and the determined site to be scanned.

Furthermore, the method may also include: adjusting the waveform of a radio frequency transmission pulse on the basis of the specific absorption rate and the root mean square value of the radio frequency field.

While the present invention has been described in detail with reference to specific embodiments, it would be understood by those skilled in the art that many modifications and variations can be made to the present invention. Therefore, it should be understood that the claims are intended to cover all such modifications and variations within the true spirit and scope of the present invention.

The invention claimed is:

1. A magnetic resonance scanning control method, comprising:
   acquiring a three-dimensional body model of a scan subject;
   estimating, on the basis of the three-dimensional body model, a value of a first body parameter and a value of a second body parameter of the scan subject;
   determining a specific absorption rate on the basis of a site to be scanned of the scan subject, the value of the first body parameter and the value of the second body parameter;
   determining an implant location in the three-dimensional body model;
   determining a root mean square value of a radio frequency field on the basis of the implant location and the site to be scanned; and
   adjusting a waveform of radio frequency transmission pulses based on the determined specific absorption rate and the root mean square value of the radio frequency field.

2. The method according to claim 1, wherein the first body parameter comprises weight and the second body parameter comprises height.

3. The method according to claim 1, wherein the step of determining the specific absorption rate comprises:
   determining a standard energy on the basis of a pre-acquired energy prediction model associated with the site to be scanned, wherein the energy prediction model is used to represent a correspondence relationship between the standard energy and different values of the first body parameter and different values of the second body parameter; and
   determining the specific absorption rate of a current scan on the basis of the standard energy.

4. The method according to claim 1, further comprising:
   determining, on the basis of the three-dimensional body model, the site to be scanned of the scan subject.

5. The method according to claim 1, wherein acquiring the three-dimensional body model of the scan subject comprises:
   acquiring a three-dimensional profile image of the scan subject; and
   data-fusing the three-dimensional profile image with a pre-stored standard human model to acquire the three-dimensional body model of the scan subject.

6. The method according to claim 5, wherein the scan subject positioned on a scanning table and is photographed using a camera to acquire the three-dimensional profile image of the scan subject.

7. The method according to claim 1, wherein the three-dimensional body model comprises a body portion as well as an information labeling portion, at least a portion of the information labeling portion being used to indicate a human anatomical site of the body portion.

8. A magnetic resonance scanning control method for a magnetic resonance system, the magnetic resonance system comprising a scanning table and a camera, and the method comprising:
   acquiring, by means of the camera, a three-dimensional profile image of a scan subject on the scanning table;
   acquiring a three-dimensional body model of the scan subject on the basis of the three-dimensional profile image;
   estimating a weight and a height of the scan subject on the basis of the three-dimensional body model;
   receiving a user operation instruction, so as to determine a site to be scanned in the three-dimensional body model;
   determining a specific absorption rate on the basis of the determined site to be scanned, the weight, and the height;
   receiving a user operation instruction, so as to determine an implant location in the three-dimensional body model;
   determining a root mean square value of a radio frequency field on the basis of the implant location and the determined site to be scanned; and
   adjusting a waveform of radio frequency transmission pulses on the basis of the specific absorption rate and the root mean square value of the radio frequency field.

9. A magnetic resonance system, comprising:
   a main magnet, a radio frequency coil assembly, a gradient coil assembly, and a scanning table used to bear a scan subject;
   a sequence pulse generator, used to generate a scan sequence, the scan sequence comprising radio frequency transmission pulses;
   a three-dimensional imaging apparatus; and
   a scanning controller, comprising operation instructions, the operation instructions being used to perform the following steps:

receiving a three-dimensional profile image of the scan subject acquired by means of the three-dimensional imaging apparatus;

acquiring a three-dimensional body model of the scan subject on the basis of the three-dimensional profile image;

estimating, on the basis of the three-dimensional body model, a value of a first body parameter and a value of a second body parameter of the scan subject;

determining a specific absorption rate on the basis of a site to be scanned of the scan subject, the value of the first body parameter, and the value of the second body parameter;

determining an implant location in the three-dimensional body model;

determining a root mean square value of a radio frequency field on the basis of the implant location and the site to be scanned of the scan subject; and adjusting a waveform of the radio frequency transmission pulses on the basis of the specific absorption rate and the root mean square value of the radio frequency field.

* * * * *